US008419706B2

United States Patent
Heldt et al.

(10) Patent No.: US 8,419,706 B2
(45) Date of Patent: Apr. 16, 2013

(54) FLUID PRODUCT DISPENSING DEVICE

(75) Inventors: Frédéric Heldt, Louviers (FR); Fabio Stradella, Camogli (IT); Giuseppe Stradella, Camogli (IT)

(73) Assignee: Aptar France SAS, Le Neubourg (FR)

( * ) Notice: Subject to any disclaimer, the term of this patent is extended or adjusted under 35 U.S.C. 154(b) by 1051 days.

(21) Appl. No.: 10/495,550

(22) PCT Filed: Nov. 14, 2002

(86) PCT No.: PCT/FR02/03900
§ 371 (c)(1),
(2), (4) Date: May 13, 2004

(87) PCT Pub. No.: WO03/041872
PCT Pub. Date: May 22, 2003

(65) Prior Publication Data
US 2005/0029288 A1    Feb. 10, 2005

(30) Foreign Application Priority Data

Nov. 15, 2001    (FR) .................................... 01 14794

(51) Int. Cl.
*A61M 5/32* (2006.01)
(52) U.S. Cl.
USPC ........................................................ 604/411
(58) Field of Classification Search .................... 604/86, 604/87, 200–206, 208, 214, 218, 222, 244–246, 604/411–414, 905; 239/309; 222/82
See application file for complete search history.

(56) References Cited

U.S. PATENT DOCUMENTS

| 2,153,594 | A | * | 4/1939 | Saffir | 604/203 |
| 3,368,558 | A | * | 2/1968 | Sarnoff et al. | 604/198 |
| 3,387,609 | A |   | 6/1968 | Shields |  |
| 4,623,337 | A | * | 11/1986 | Maurice | 604/298 |
| 4,643,721 | A | * | 2/1987 | Brunet | 604/191 |

(Continued)

FOREIGN PATENT DOCUMENTS

| DE | 14 91 663 A | 8/1969 |
| DE | 198 37 127 A | 5/1999 |

(Continued)

*Primary Examiner* — Tatyana Zalukaeva
*Assistant Examiner* — Benedict L Hanrahan
(74) *Attorney, Agent, or Firm* — Sughrue Mion, PLLC

(57) ABSTRACT

A fluid dispenser device comprising a body provided with a dispenser orifice, a reservoir containing at least one dose of fluid being disposed statically in said body, said reservoir being closed in sealed manner by two stoppers, a first stopper and a second stopper the fluid being disposed in a fluid chamber, said device further comprising opener means for opening said first stopper, said opener means being disposed statically in said body, actuator means being connected to said second stopper, the actuation of said second stopper creating pressure in the fluid chamber; said pressure displacing and/or deforming said first stopper towards said opener means, and then fluid is expelled through said open first stopper towards said dispenser orifice, a spray profile being provided downstream from said dispenser orifice, the device further comprising precompression means.

11 Claims, 5 Drawing Sheets

U.S. PATENT DOCUMENTS

| | | | | |
|---|---|---|---|---|
| 4,767,416 A | * | 8/1988 | Wolf et al. | 604/239 |
| 4,905,899 A | * | 3/1990 | Coombs et al. | 239/11 |
| 4,936,841 A | * | 6/1990 | Aoki et al. | 604/413 |
| 5,637,087 A | * | 6/1997 | O'Neil et al. | 604/82 |
| 6,450,216 B1 | * | 9/2002 | Stradella | 141/27 |
| 6,569,124 B1 | * | 5/2003 | Perouse | 604/198 |
| 6,626,379 B1 | * | 9/2003 | Ritsche et al. | 239/337 |
| 6,893,423 B2 | * | 5/2005 | Denolly | 604/192 |
| 6,964,381 B2 | * | 11/2005 | Stradella et al. | 239/333 |

FOREIGN PATENT DOCUMENTS

| | | | |
|---|---|---|---|
| EP | 0 546 607 A | | 6/1993 |
| FR | 2 809 628 | * | 12/2001 |
| FR | 2809628 A1 | * | 12/2001 |
| FR | 2 847 834 | * | 6/2004 |
| WO | WO 01 30423 A | | 5/2001 |

* cited by examiner

FLUID PRODUCT DISPENSING DEVICE

The present invention relates to a fluid dispenser device, and more particularly to such a device designed to dispense a small number of doses, such as a single-dose or a two-dose device.

Fluid dispenser devices which contain only a few doses must be capable of being made at low cost, while guaranteeing that the fluid is stored and dispensed safely and reliably.

Documents WO 95/27568 and EP-0 546 607 disclose two devices of that type. The device of document WO 95/27568 includes a reservoir provided with a single opening which is closed by a piercable stopper. A piercing needle is secured to the body, and during actuation, the body and the needle are displaced together relative to the reservoir towards the stopper so as to pierce it, the stopper then being driven in displacement inside the reservoir, and thus being transformed into a piston so as to dispense the contents of the reservoir through said needle. The device of document EP-0 546 607 is similar, i.e. it also includes a piercing needle secured to the body. Compared with the first above-mentioned document, the difference is that, in the second device, it is the reservoir that is displaced by the user relative to said head so that during actuation, the stopper is firstly pierced, and then displaced inside the reservoir, transforming itself into a piston so as to dispense the fluid through the needle.

In the two above-mentioned examples, the reservoir is closed by a stopper which transforms into a piston after said stopper has been pierced. In addition, the reservoir is always mounted to move relative to the body so as to enable the piston to be displaced inside the reservoir while dispensing fluid. This implies that the device is relatively complicated to assemble and to refill.

Documents DE-1 491 663, U.S. Pat. No. 3,387,609, and WO 01/30423 disclose syringes. In that type of dispenser, any precompression of the fluid is harmful and undesirable for the user. The same applies to document U.S. Pat. No. 4,623,337 which discloses an eye-drop dispenser.

An object of the present invention is to provide a different fluid dispenser device which is simple and inexpensive to manufacture and to assemble.

Another object of the present invention is to provide such a fluid dispenser device in which filling the reservoir with fluid is simplified.

Another object of the present invention is to provide such a device which guarantees that the fluid is fully converted into spray, and that the entire dose of fluid is dispensed.

The present invention thus provides a fluid dispenser device comprising a body provided with a dispenser orifice, a reservoir containing at least one dose of fluid being disposed statically in said body, said reservoir being closed in sealed manner by two stoppers, a first stopper and a second stopper, the fluid being disposed in a fluid chamber situated between said first and second stoppers, said device further comprising opener means for opening said first stopper, said opener means being disposed statically in said body, actuator means being connected to said second stopper so as to displace it in said reservoir, the actuation of said second stopper creating pressure in the fluid chamber; said pressure displacing and/or deforming said first stopper towards said opener means, in such a manner that firstly said first stopper is opened, and then fluid is expelled through said open first stopper towards said dispenser orifice, a spray profile being provided upstream from said dispenser orifice, the device further comprising precompression means so as to create precompression in the reservoir before said first stopper is opened by said opener means, so as to improve the spraying of the fluid, and so as to ensure that the entire dose of fluid is dispensed.

Said opener means for opening the first stopper advantageously comprise a hollow needle designed to pierce said first stopper and to transfer the fluid towards the dispenser orifice.

In a first variant embodiment, said first stopper is disposed inside said reservoir and is displaceable towards said opener means during actuation.

In a second variant embodiment, said first stopper is fixed to said reservoir by a fixed portion, and includes a deformable portion that is disposed inside said reservoir, and that deforms towards said opener means during actuation.

Said fixed portion of the first stopper is advantageously fixed on the outside of the reservoir.

In a first embodiment of the invention, said reservoir contains a single dose of fluid that is dispensed during a single actuation of the device.

In a second embodiment of the invention, said reservoir contains at least two doses of fluid that are dispensed during successive actuations of the device, said actuator means including dose-fractioning means.

Said precompression means are advantageously formed on the first stopper, and/or on the opener means, and/or on the reservoir.

Said precompression means advantageously comprise resistance means requiring an actuating force that is greater than a predetermined threshold in order to open said first stopper.

Said resistance means advantageously comprise an abutment co-operating with said first stopper before it is opened, said first stopper being deformable in order to be capable of moving past said abutment.

Other characteristics and advantages of the present invention appear more clearly from the following detailed description of two variant embodiments thereof, made with reference to the accompanying drawings, and given as non-limiting examples, in which.

Figure 2:
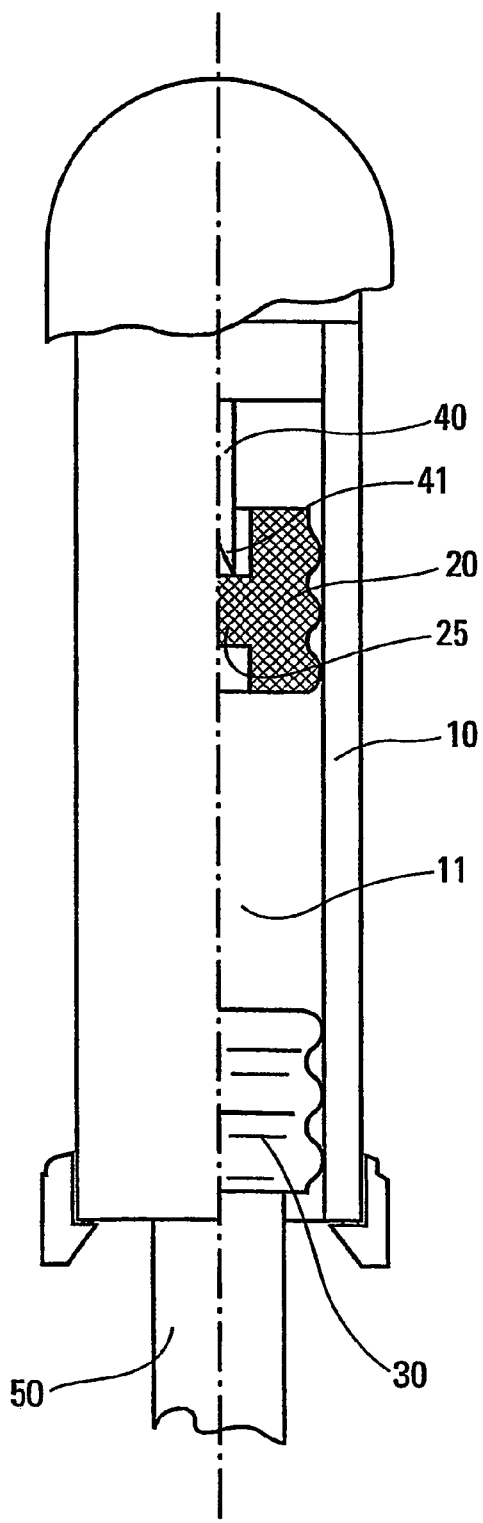
FIGS. 2 and 3 are large-scale diagrammatic views of a reservoir constituting a first variant embodiment of the present invention, shown respectively before and after actuation.
Figure 3:
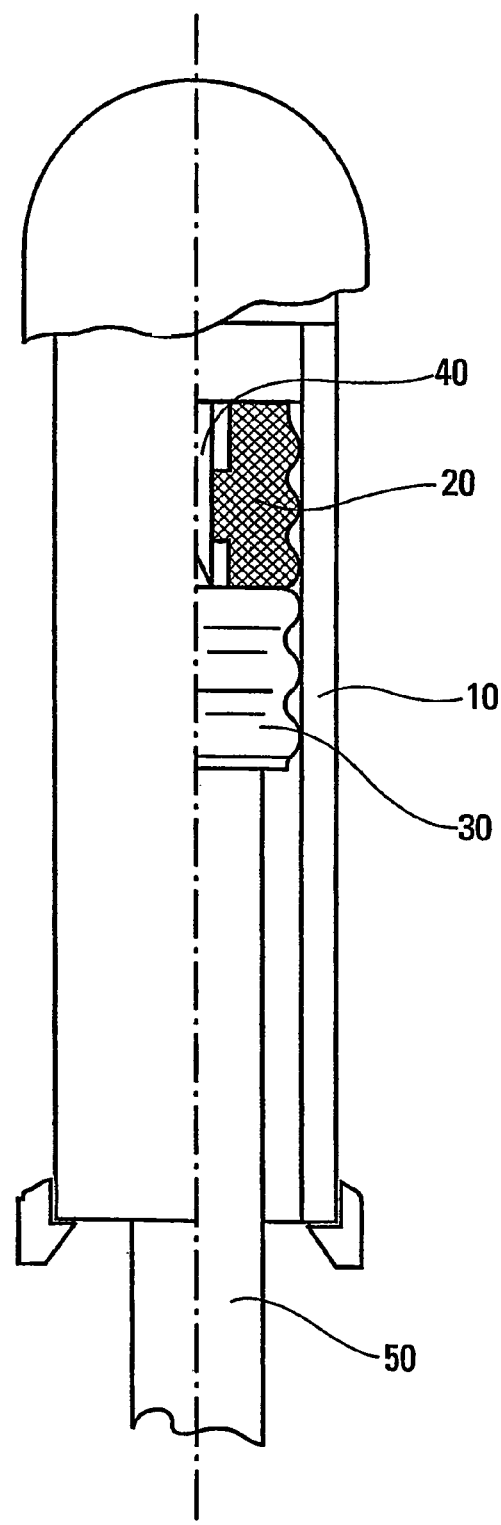
Figures 4, 5:
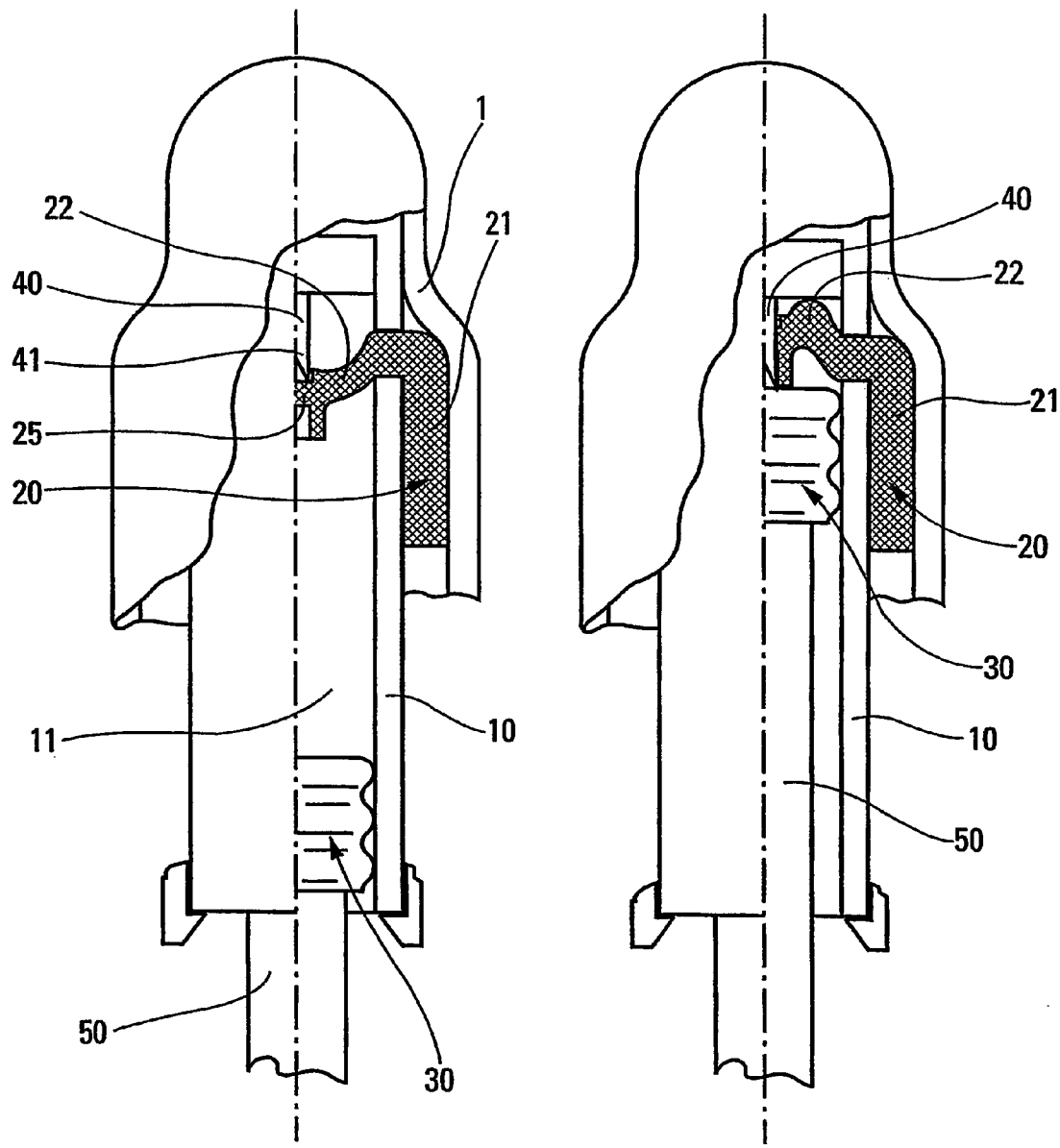

FIGS. 4 and 5 are views similar to the views in FIGS. 2 and 3, showing a second variant embodiment of the present invention, shown respectively before and after actuation of the device; and FIGS. 6, 7, 8, and 9 show various variant embodiments of the present invention.

Figure 1:
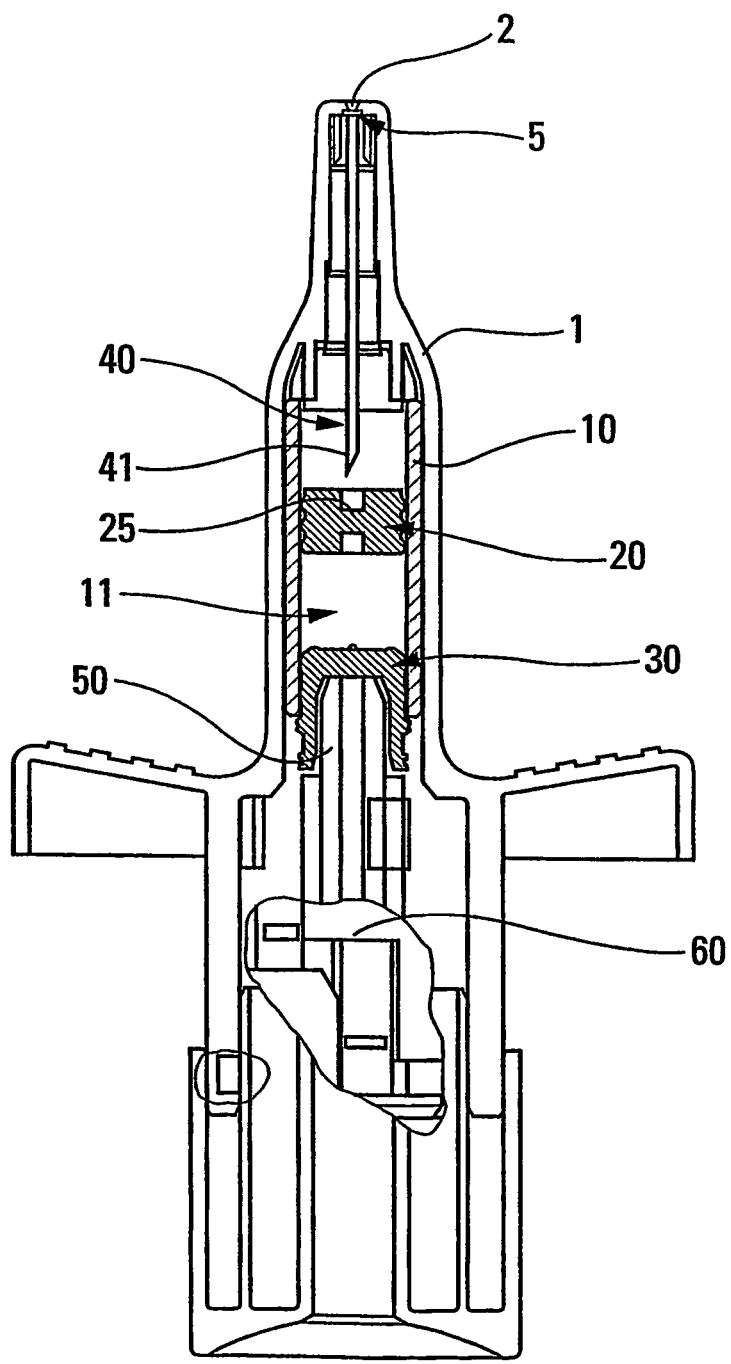
FIG. 1 is a diagrammatic cross-section view of a fluid dispenser device of a particular embodiment of the present invention, before actuation.

With reference to FIG. 1, which shows a dispenser device of the two-dose type, i.e. containing two doses of fluid in the reservoir, the device comprises a body 1 which incorporates the dispenser orifice 2 and which contains a reservoir 10. The reservoir 10 is disposed-statically relatively to said body 1. The reservoir is open at both ends, and is therefore closed in sealed manner by a first stopper 20 disposed at one end of the reservoir 10, and by a second stopper 30 disposed at the other end of said reservoir 10. A fluid chamber 11 is therefore defined between said stoppers 20 and 30, the fluid chamber 11 containing the fluid to be dispensed.

Opener means 40 are provided for opening the first stopper 20, which opener means are advantageously provided in the form of a piercing needle 40. The piercing needle 40 is preferably connected directly to the dispenser orifice 2, and formed with a first end pointing inward and away from the dispenser orifice 2 and having a piercing point 41 at the first end designed to pierce the stopper 20, preferably in an opening portion 25 thereof. The needle 40 is preferably hollow so that once the stopper 20 is pierced, the fluid flows inside the needle 40 towards an opposite second end and towards the dispenser orifice 2. In the invention, the spray profile 5 is provided upstream from the dispenser orifice 2, so as to dispense the fluid in the form of a fine spray.

The second stopper 30 is connected to an actuator device 50, which can be a manual actuator device which the user presses so as to dispense the fluid. The stopper 30 is mounted in displaceable manner inside the reservoir 10, so that when the user presses on the actuator device 50, said actuator device exerts an axial force on the second stopper 30. The axial force creates pressure inside the fluid chamber 11, and since the fluid is incompressible, this pressure is transmitted to the first stopper 20, and displaces said first stopper towards the needle 40. Thus, the first stopper 20 is initially pierced by the needle 40, then, under the effect of the axial force exerted by the user, the fluid contained in the fluid chamber 11 is dispensed through said needle 40 towards the dispenser orifice 2.

Figure 6:
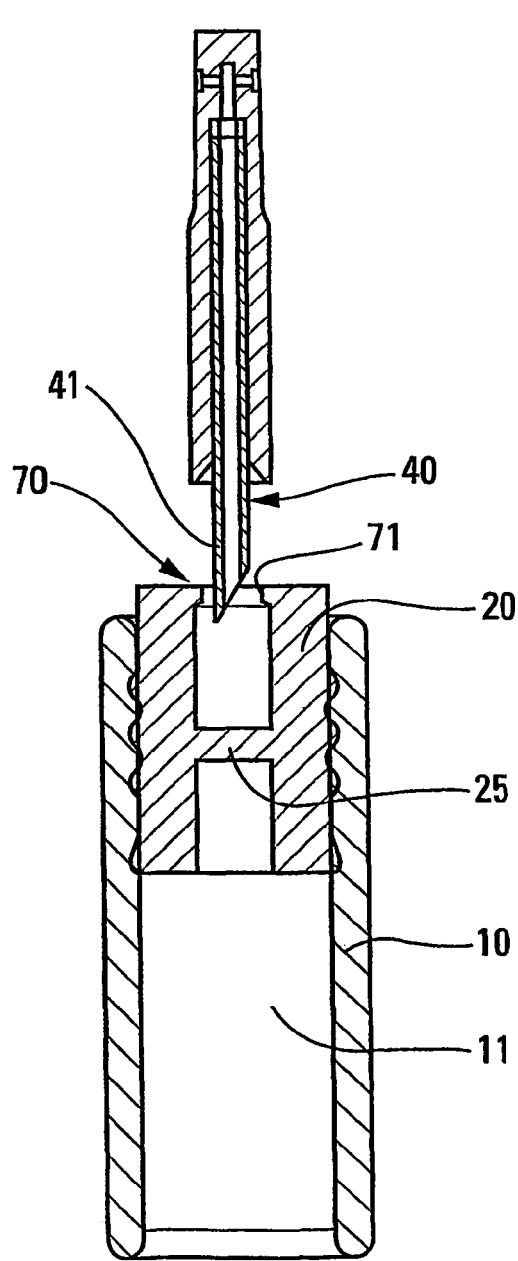
Figure 7:
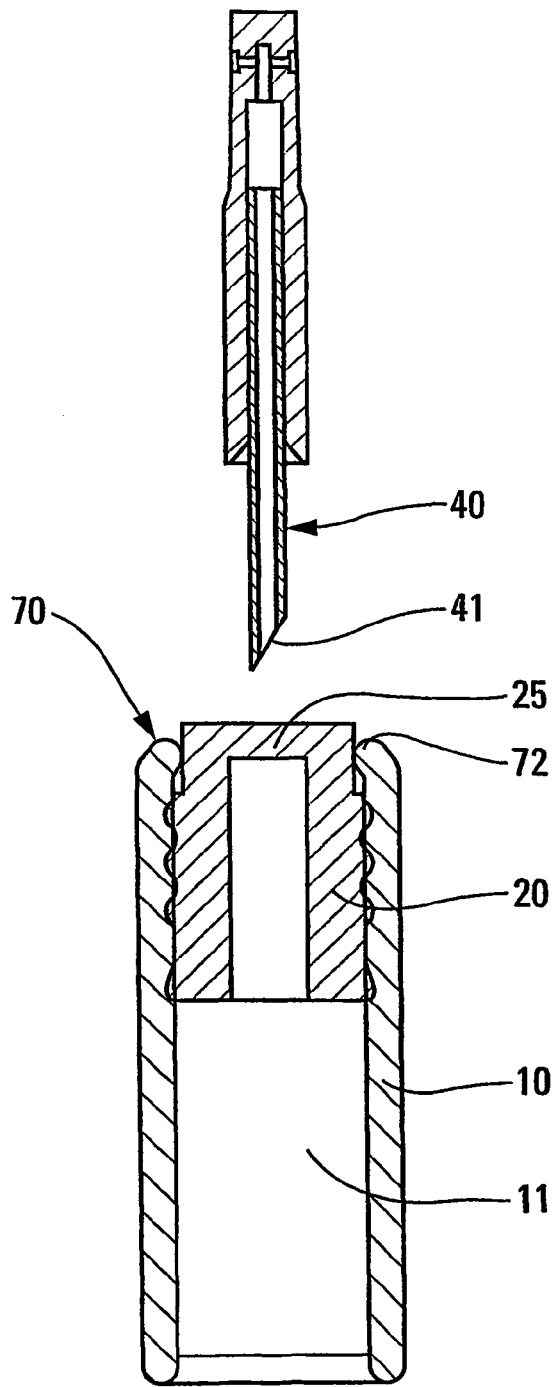
Figure 8:
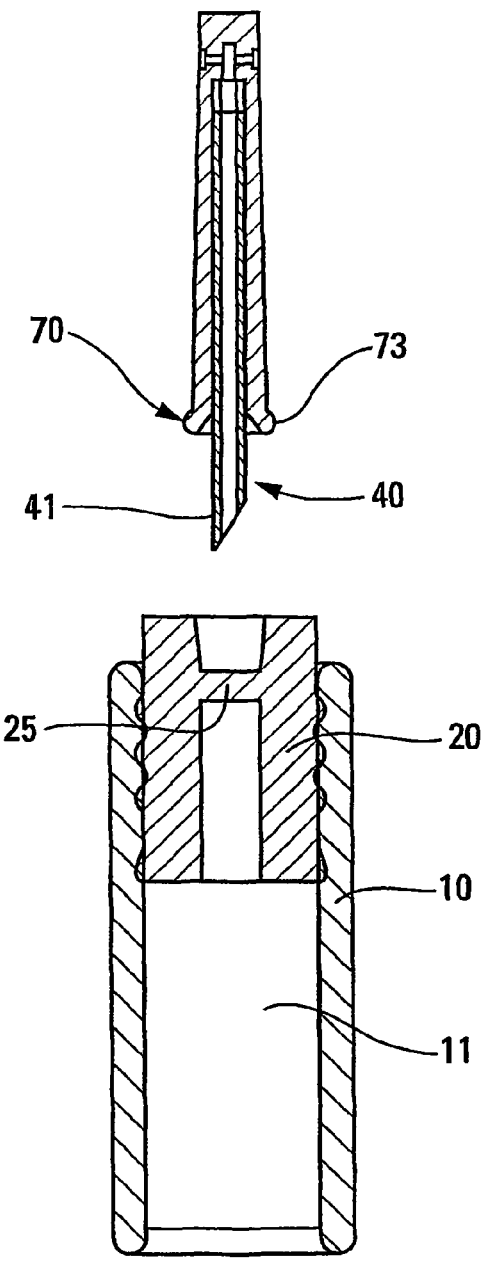
Figure 9:
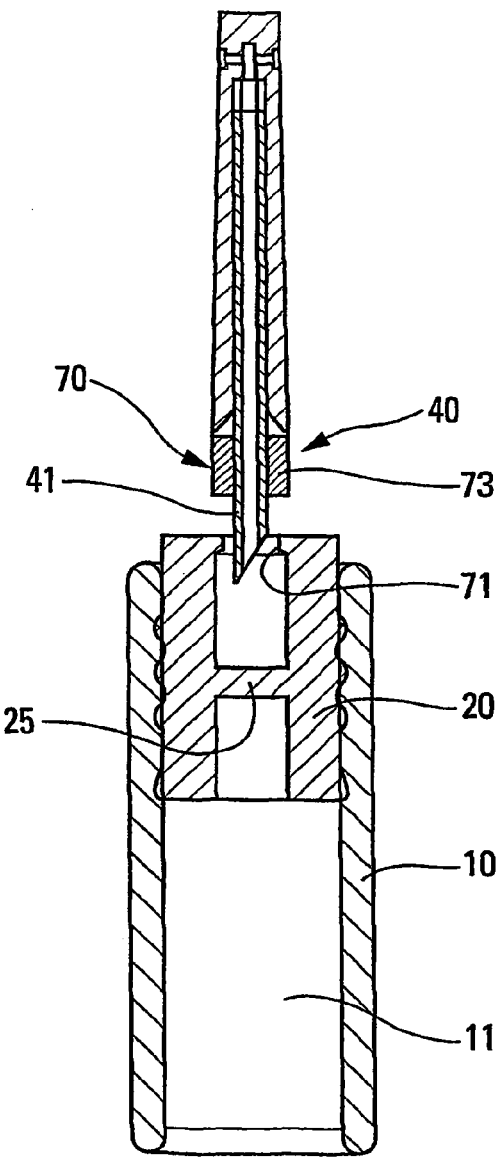

In the invention, precompression means are provided in order to create precompression before the first stopper 20 is opened. This favors good spraying of the fluid. In addition, this also causes energy to be accumulated in the hand of the user during actuation. This phenomenon also favors good spraying of the fluid, and guarantees that each dose of fluid is dispensed in its entirety, which is not always the case in devices that do not cause energy to be accumulated in the hand of the user and/or do not precompress the fluid before dispensing. The precompression means 70 can be formed on the first stopper 20, as shown in FIG. 6, on the reservoir 10, as shown in FIG. 7, or on the opener means 40, as shown in FIGS. 8 and 9. Naturally, the means can be combined together, as shown in particular in FIG. 9. They can include resistance means or zones 71, 72, 73, advantageously forming an abutment, and causing the stopper 20 to become deformed so as to be able to move past them. Advantageously, this makes it possible to predetermine the threshold level of force needed to actuate the device, even though the friction of the stopper in the reservoir is a parameter that is difficult to control.

The device of the present invention therefore provides a body 1 containing a reservoir 10, the reservoir 10 being fixed to the inside of the body 1, the body 1 also incorporating the opener means 40 for opening the first stopper 20, in this case the piercing needle 40, the needle therefore also being static relative to said reservoir 10. Only the stoppers 20 and 30 are movable inside the reservoir 10. The stopper 20 is pierced during actuation, and it is the stopper 30 which acts as a piston so as to dispense the fluid.

In addition to making the reservoir simpler to install in the device, since said reservoir is static in the body 1 and must not be displaceable relative to said body during actuation, a particular advantage of this embodiment is that the reservoir is easier to fill. The reservoir 10 of the invention can be assembled in the body 1, then the first stopper 20 can be inserted therein. Finally, the reservoir can be filled in very simple manner with the fluid, upstream from said stopper 20, and the reservoir can be finally plugged in sealed manner by the second stopper 30. The actuator system 50 can then be assembled on the body 1, with it being possible to do this at any moment since the reservoir is closed in sealed manner, once the second stopper 30 has been put in place. Prior-art devices in which the reservoir is closed by a single stopper only, and which is transformed, after being pierced, into a piston, cannot be filled in this way.

The embodiment shown in FIG. 1 is a two-dose device. The actuator system 50 advantageously includes dose-fractioning means 60, which, in this embodiment, are provided by an abutment 60 which limits the stroke of the piston (second stopper) 30 during the first actuation. The actuator system 50 must then be displaced relative to said abutment 60, e.g. turned about the central axis of the device, so as to be able to dispense the second dose. Naturally, the present invention also applies to single-dose devices, i.e. containing only a single dose of fluid dispensed in a single actuation. It is also possible to envisage providing more than two doses, e.g. three or four. In addition, FIG. 1 shows an actuator system 50 on which the user exerts an axial force so as to dispense the fluid. In a variant, it is possible to provide a laterally-actuated system in which the user exerts an actuating force in a direction that is different from the displacement direction of the piston (second stopper) during dispensing.

FIG. 1 shows opener means 40 provided in the form of a hollow needle, but the opener means 40 could be provided in some other form, e.g. in the form of a hollow tube which serves to displace a closure element held in the opening portion 25 of the first stopper 20, e.g. a bead or the like. In this case, the closure element is displaced by the opener means 40 during actuation of the device, and the fluid is then dispensed through said hollow tube. This embodiment is not shown in the drawings, but it could very well be applied to the present invention. Other variants of the opener means can also be envisaged.

FIGS. 2 and 3 are large-scale views of the reservoir constituting a first variant similar to the embodiment shown in FIG. 1. In this first variant, the first stopper 20 is disposed inside the reservoir 10, and slides over the inside wall of said reservoir 10 when the user actuates the actuator system 50 so as to dispense the fluid. In this variant, it is therefore the entire first stopper 20 which is displaced relative to the reservoir, so as to be opened, in particular pierced, by the opening device 40.

In a variant, FIGS. 4 and 5 show a first stopper 20 which is not displaceable, but is deformable relative to the reservoir 10. To this end, the first stopper 20 includes a fixed portion 21 which is fixed to the reservoir 10, and a deformable portion 22 which is designed to deform towards the opener means 40 during actuation of the device. The static portion 21 can advantageously be secured to the outside of the reservoir 10, while the deformable portion, disposed inside the reservoir 10, incorporates the opening portion 25 which comes to cooperate with the opener means 40, in this case the point 41 of the needle 40. As can be seen in FIG. 4, the deformable portion 22 of the first stopper 20 can include a bend that is directed downwards in FIG. 4, said bend providing resistance that is greater than the force needed to deform the deformable portion 22 during actuation. This also favors precompression and/or the accumulation of energy in the hand of the user. It is also possible to envisage providing a first stopper that is both displaceable and deformable.

The present invention is described above with reference to a plurality of variant embodiments, but it is clear that it is not limited to those variants. On the contrary, a person skilled in the art can apply any desired modifications thereto without going beyond the ambit of the present invention as defined by the accompanying claims.

The invention claimed is:

1. A nasal spray device, comprising:
a body (1) configured to be inserted into a nasal passage for dispensing fluid in the nasal passage and provided with a dispenser orifice (2),
a reservoir (10) containing at least one dose of fluid being disposed statically in said body (1), said reservoir (10) including a cylindrical wall distinct from and disposed entirely inside the body such that the body does not define a fluid sealing surface of the reservoir, said reservoir being closed in sealed manner by a first stopper (20) and a second stopper (30), the fluid being disposed in a fluid chamber (11) formed by said first and second stoppers (20, 30) and said cylindrical wall,
opener means (40) for opening said first stopper (20), said opener means (40) being disposed statically in said body (1),
actuator means (50) being connected to said second stopper (30) so as to displace said second stopper in said reservoir (10), the actuation of said second stopper (30) creating pressure in the fluid chamber (11), said pressure displacing and/or deforming said first stopper (20) towards said opener means (40), in such a manner that firstly said first stopper (20) is opened, and then fluid is expelled through said open first stopper (20) towards said dispenser orifice (2),
a spray profile (5) provided upstream from said dispenser orifice (2) to dispense the fluid in the form of a fine spray; and
precompression means (70) to create precompression in the reservoir (10) before said first stopper (20) is opened by said opener means (40), so as to improve the spraying of the fluid, and so as to ensure that the entire dose of fluid is dispensed,
wherein said opener means for opening the first stopper comprise a hollow needle in which only one end has a sharp point, pointing away from the dispensing orifice,
wherein the sharp point is formed by a bevel, and the needle has the bevel at only the first end that forms the sharp point.

2. A device according to claim 1, in which said a hollow needle (40) is designed to pierce said first stopper (20) and to transfer the fluid towards the dispenser orifice (2).

3. A device according to claim 1, in which said first stopper (20) is disposed inside said reservoir (10) and is displaceable towards said opener means (40) during actuation.

4. A device according to claim 1, in which said reservoir (10) contains a single dose of fluid that is dispensed during a single actuation of the device.

5. A device according to claim 1, in which said reservoir (10) contains at least two doses of fluid that are dispensed during successive actuations of the device, said actuator means (50) including dose-fractioning means (60).

6. A device according to claim 1, in which said precompression means (70) are formed on the first stopper (20), and/or on the opener means (40), and/or on the reservoir (10).

7. A device according to claim 6, in which said precompression means (70) comprise resistance means (71, 72, 73) requiring an actuating force that is greater than a predetermined threshold in order to open said first stopper (20).

8. A device according to claim 7, in which said resistance means (70) comprise an abutment co-operating with said first stopper (20) before it is opened, said first stopper (20) being deformable in order to be capable of moving past said abutment.

9. A nasal spray device comprising:
a body specifically configured to be inserted into a nasal passage for dispensing fluid in the nasal passage, said body forming a dispenser orifice and a spray profile;
a reservoir containing at least one dose of fluid being disposed in said body, said reservoir being closed in sealed manner by a first stopper and a second stopper, wherein the reservoir comprises a cylindrical wall distinct from and disposed entirely inside the body such that the body does not define a fluid sealing surface of the reservoir, the fluid being disposed in a fluid chamber formed by said first and second stoppers and said cylindrical wall;
opener means for opening said first stopper, said opener means being disposed entirely inside said body;
actuator means connected to said second stopper so as to displace said second stopper in said reservoir in a direction toward said dispenser orifice, the actuation of said second stopper creating pressure in the fluid chamber, said pressure displacing and/or deforming said first stopper in a direction towards said opener means and dispenser orifice, in such a manner that firstly said first stopper is opened, and then fluid is expelled through said open first stopper towards said dispenser orifice,
wherein said spray profile is provided upstream from said dispenser orifice to dispense the fluid in the form of a fine spray; and
precompression means so as to create precompression in the reservoir before said first stopper is opened by said opener means, so as to improve the spraying of the fluid, and so as to ensure that the entire dose of fluid is dispensed,
wherein said opener means comprise a needle having a first end that points inwards and away from the dispenser orifice, a second end opposite from the first end, wherein only the first end has a sharp point,
wherein the sharp point is formed by a bevel, and the needle has the bevel at only the first end that forms the sharp point.

10. The device according to claim 1, wherein actuating surfaces for a user's fingers are formed integrally with the body.

11. A nasal spray device comprising:
a body specifically configured to be inserted into a nasal passage for dispensing fluid in the nasal passage, said body comprising a cylindrical interior wall, a dispenser orifice, and a spray profile, wherein the spray profile is disposed upstream from the dispenser orifice to dispense fluid passing therethrough in the form of a fine spray;
a reservoir comprising at least one dose of fluid, the reservoir comprising a cylindrical wall and disposed entirely within the cylindrical interior wall of the body so as to be distinct from the body, and wherein the reservoir is sealed by two stoppers, a first stopper and a second stopper, and the fluid is contained between the first and second stoppers;
a piercing needle that is structured to open the first stopper, the piercing needle disposed entirely within the body, in a location upstream from the dispenser orifice and downstream from the first and second stoppers before actuation of an actuator;
said piercing needle having a first end that points inwards and away from the dispenser orifice, a second end that is opposite from the first end, and a sharp point provided only on the first end;
said actuator connected to the second stopper so as to displace the second stopper within the reservoir, the displacement of the second stopper creating pressure in the fluid chamber that displaces, deforms or displaces and deforms the first stopper towards the piercing needle so that the first stopper is opened and fluid is then expelled through the first stopper towards the dispenser orifice; and precompression means for creating precompression in the reservoir before the first stopper is opened by the piercing needle, wherein the sharp point is formed by a bevel, and the needle has the bevel at only the first end that forms the sharp point.

* * * * *